(12) United States Patent
Al Jabri

(10) Patent No.: US 10,989,618 B2
(45) Date of Patent: Apr. 27, 2021

(54) INDUSTRIAL GAS DETECTION

(71) Applicant: Saudi Arabian Oil Company, Dhahran (SA)

(72) Inventor: Khalid Rasheed Al Jabri, Abha (SA)

(73) Assignee: Saudi Arabian Oil Company, Dhahran (SA)

( * ) Notice: Subject to any disclaimer, the term of this patent is extended or adjusted under 35 U.S.C. 154(b) by 393 days.

(21) Appl. No.: 16/014,208

(22) Filed: Jun. 21, 2018

(65) Prior Publication Data

US 2019/0391034 A1    Dec. 26, 2019

(51) Int. Cl.
*G01M 3/04* (2006.01)

(52) U.S. Cl.
CPC ..................................... *G01M 3/04* (2013.01)

(58) Field of Classification Search
CPC . G01M 3/04; G01N 33/0044; G01N 33/0067; G01N 33/0031
See application file for complete search history.

(56) References Cited

U.S. PATENT DOCUMENTS

| | | | |
|---|---|---|---|
| 9,799,196 B1 | 10/2017 | Boushehri et al. | |
| 2011/0316699 A1 | 12/2011 | Arunchalam | |
| 2018/0299417 A1* | 10/2018 | Cha | G01N 33/0067 |

FOREIGN PATENT DOCUMENTS

| | | |
|---|---|---|
| CA | 2612778 | 1/2007 |
| CN | 201662876 | 12/2010 |
| DE | 4001959 | 7/1991 |
| GB | 2259572 | 3/1993 |
| WO | 2017082609 | 5/2017 |

OTHER PUBLICATIONS fireandgassystems.com' [online], "S4000CH Intelligent Sensor for Combustible Gas Detector," available on or before Apr. 21, 2017, [retrieved on Jun. 22, 2018], retrieved from URL: <http://www.fireandgassystems.com/products/combustible_s4000ch.html>, 2 pages.
digi.com [online], available on or before May 7, 2018, [retrieved on Jun. 22, 2018], retrieved from URL: <https://www.digi.com/xbee>, 15 pages.
International Search Report and Written Opinion issued in International Application No. PCT/US2019/038424 dated Oct. 15, 2019, 11 pages.
GCC Examination Report in GCC Appln. No. GC 2019-37796, dated Jun. 29, 2020, 3 pages.

* cited by examiner

*Primary Examiner* — Manuel A Rivera Vargas
(74) *Attorney, Agent, or Firm* — Fish & Richardson P.C.

(57) ABSTRACT

Methods, systems, and computer-readable medium to perform operations comprising identifying a first gas level of a gas at a first location at a first time; determining that the first gas level of the gas is above a first threshold; in response to determining that the first gas level of the gas is above the first threshold, identifying a second gas level of the gas at a second location at a second time; determining that the second gas level of the gas is above a second threshold; in response to determining that the second gas level of the gas is above the second threshold, calculating a difference between the second time and the first time; based on the difference, determining that one of the first location and the second location as a source of the gas; and providing an alert based on determining the location of the source of the gas.

20 Claims, 8 Drawing Sheets

INDUSTRIAL GAS DETECTION

TECHNICAL FIELD

This disclosure relates to industrial gas detection.

BACKGROUND

There are many situations in which hazardous gases may accumulate in dangerous concentrations in or near facilities. In such cases, accumulations of such hazardous gases should be detected before a hazardous situation exists. For example, many industrial processes use highly flammable or poisonous gases that should be detected.

SUMMARY

The present disclosure discusses detection of industrial gases using portable sensors and logging. Specifically, the portable gas sensors are installed proximate to a facility, such as an industrial plant, to detect industrial gas levels (for example, $H_2S$, $NH_3$, CO, LEL, greenhouse gasses). The gas sensors can transmit data of the detected gas levels wirelessly to be further processed, for example, to a gas detection computing unit located at a plant operator's room. The gas detection computing unit can share the gas level readings with network members, and further generate automated alerts to radio terminals and operators when gas levels exceed normal levels.

Innovative aspects of the subject matter described in this specification may be embodied in methods that include the actions of identifying a first gas level of a gas at a first location at a first time; determining that the first gas level of the gas is above a first threshold; in response to determining that the first gas level of the gas is above the first threshold, identifying a second gas level of the gas at a second location at a second time; determining that the second gas level of the gas is above a second threshold; in response to determining that the second gas level of the gas is above the second threshold, calculating a difference between the second time and the first time; based on the difference between the second time and the first time, determining that one of the first location and the second location as a source of the gas; and providing an alert based on determining the location of the source of the gas.

Other embodiments of these aspects include corresponding systems, apparatus, and computer programs, configured to perform the actions of the methods, encoded on computer storage devices.

These and other embodiments may each optionally include one or more of the following features. For instance, calculating the difference between the second time and the first time includes determining that the difference is positive, in response to determining that the difference is positive, determining that the first location is the source of the gas; and providing the alert indicating that the first location is the source of the gas. Calculating the difference between the second time and the first time includes determining that the difference is negative, in response to determining that the difference is negative, determining that the second location is the source of the gas; and providing the alert indicating that the second location is the source of the gas. Determining that the second gas level of the gas is below the second threshold; and in response to determining that second gas level of the gas is below the second threshold, providing an alert indicating that the first gas level is above the first threshold. The alert is an auditory alert. The gas includes hydrogen sulfide. Storing, in a data store, data indicating i) the first location and the first gas level of the gas and ii) the second location and the second gas level of the gas. The first and second gas levels are respective percentages of the gas in a sampled quantity of ambient air. The first location differs from the second location.

Particular implementations of the subject matter described in this specification can be implemented so as to realize one or more of the following advantages. For example, implementation of the subject matter mitigate the excess use of hundreds of meters of power and signaling hardwiring for running remote gas sensors. Further, the subject matter provides detection of leak direction of industrial gases from neighboring plant(s), facilitating identification of where and which plant contributes to pollute the area with industrial gases.

The details of one or more implementations of the subject matter described in this disclosure are set forth in the accompanying drawings and the description herein. Other features, aspects, and advantages of the subject matter will become apparent from the description, the drawings, and the claims.

DETAILED DESCRIPTION

Figure 1:
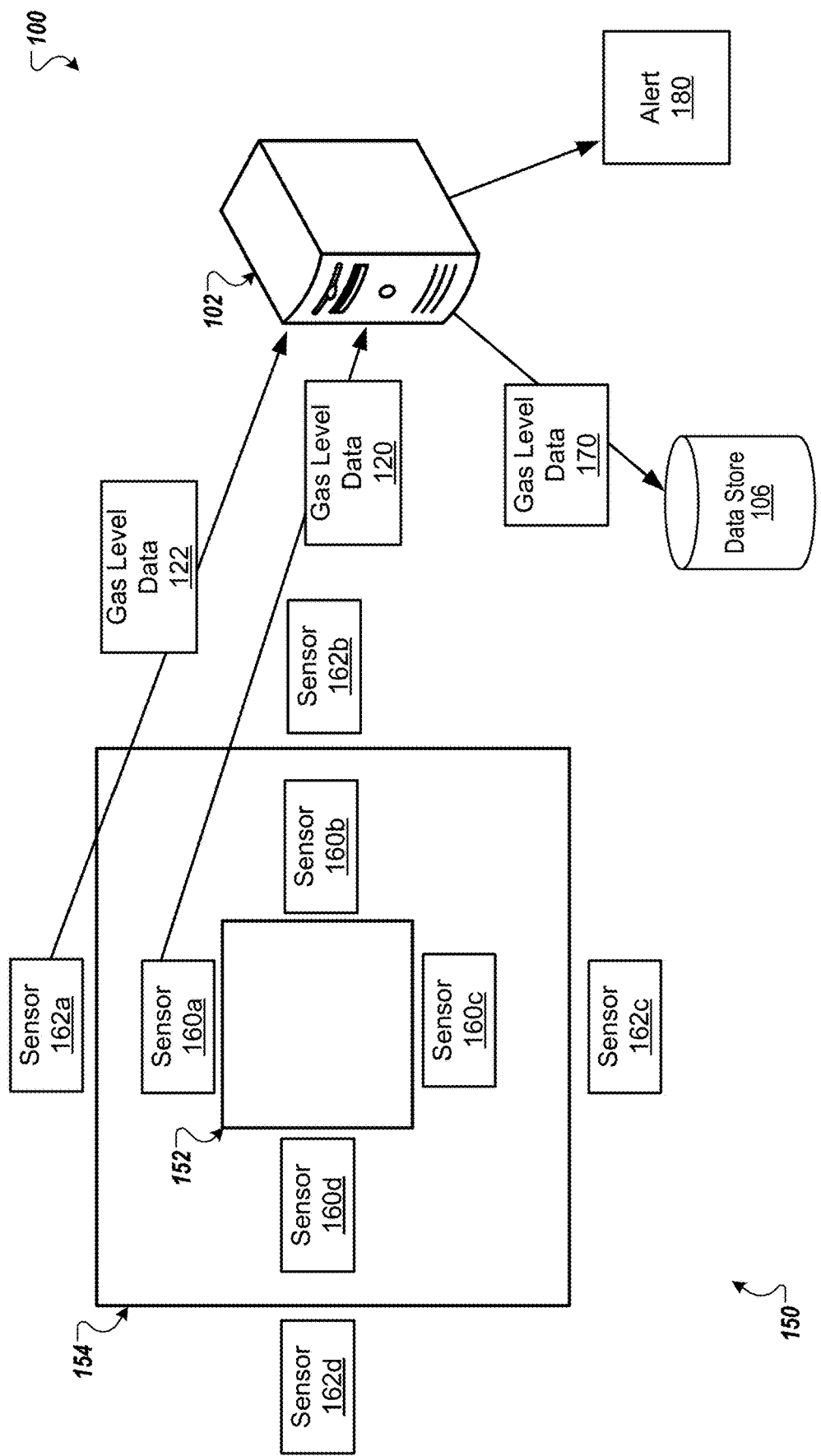
FIG. 1 is a schematic illustration of a system for detecting industrial gases.

The present disclosure describes a computing system 100 for detecting industrial gases, shown in FIG. 1. The computing system 100 includes a computing device 102 that can be in communication with one or more other computing systems (not shown) over one or more networks (not shown). The system 100 further includes a data store 106, with the computing device 102 in communication with the data store 106.

FIG. 1 further illustrates a facility 150 that is exposed to high emission levels of gases. In some examples, high emission levels of gases are abnormal gas levels which can cause direct life threat to anyone that could be working inside or nearby the facility 150 (e.g., a petrochemical facility). Specifically, the facility 150 can include a first perimeter 152 and a second perimeter 154 surrounding the first perimeter 152. The facility 150 can further include gas sensors 160*a*, 160*b*, 160*c*, 160*d* (collectively referred to as gas sensors 160) positioned around the first perimeter 152; and can further include gas sensors 162*a*, 162*b*, 162*c*, 162*d* (collectively referred to as gas sensors 162) positioned around the second perimeter 154. The gas sensors 160 and 162 can detect gas levels of one or more gases at locations of the respective gas sensors 160, 162 (each of the locations of the gas sensors 160, 162 differing). In some examples, the detected gas levels are respective percentages of the gas in a sampled quantity of ambient air proximate to the location of the gas sensor 160, 162. In some examples, the gas includes hydrogen sulfide. In some examples, a high emission level of hydrogen sulfide can be between 10 ppm to 99 ppm, or greater than 100 ppm.

Each of the gas sensors 160 can be "paired" with one of the gas sensors 162. Specifically, each of the gas sensors 160 can be associated with one of the gas sensors 162 based on one or more parameters—for example, distance or direction. For example, the gas sensor 160a is associated with the gas sensor 162a as the gas sensor 162a is the closest to the gas sensor 160a. Similarly, the gas sensor 160b is associated with the gas sensor 162b; the gas sensor 160c is associated with the gas sensor 162c, and the gas sensor 160d is associated with the gas sensor 162d. The facility 150 can include any number of gas sensors.

The computing device 102 further includes a gas level receiver (not shown). The receiver can (wirelessly) receive data transmitted by each of the gas sensors 160, 162, including data indicating gas levels of gases proximate to the location of the respective sensors 160, 162.

Figure 2:
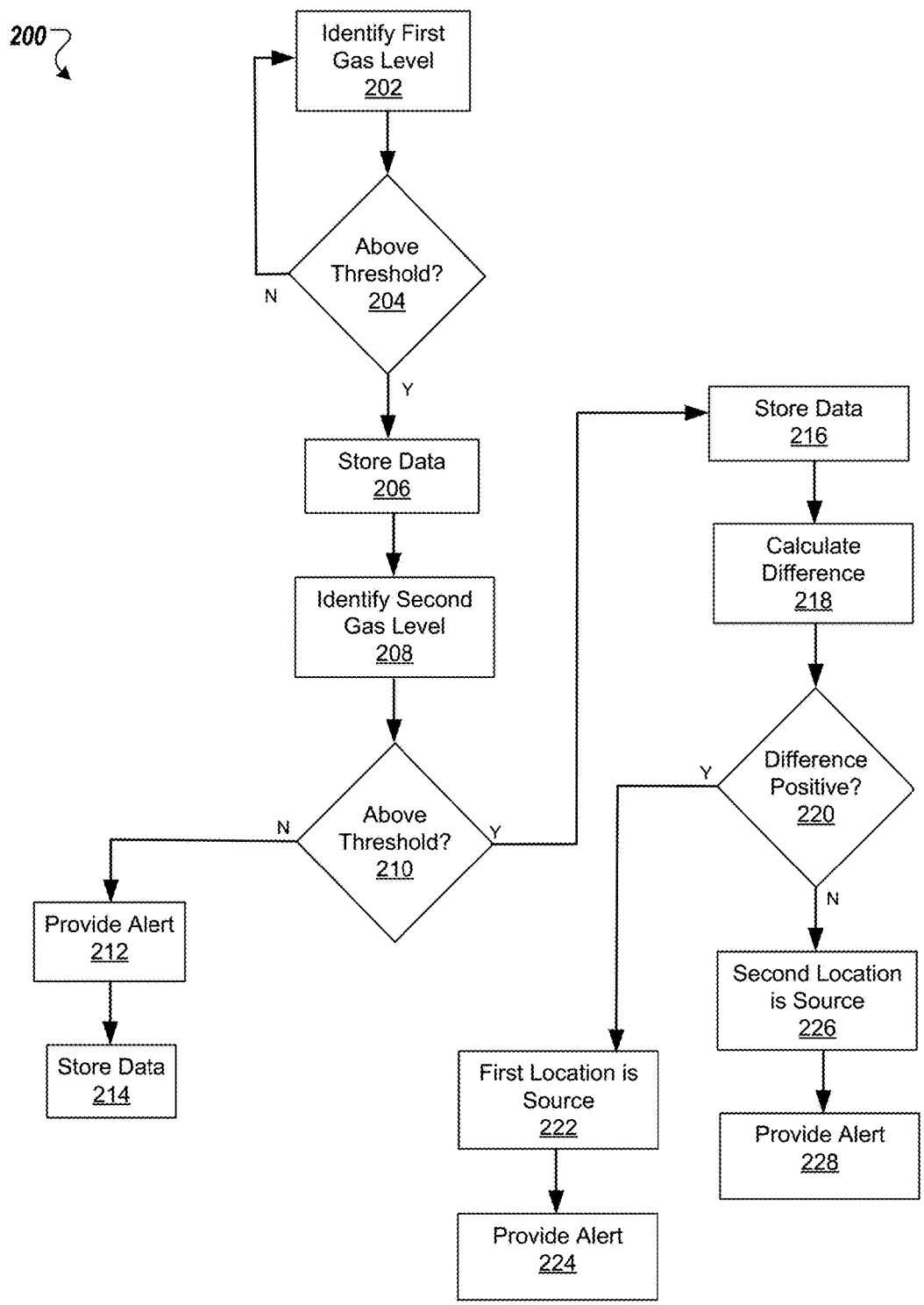
FIG. 2 illustrates a flowchart for detecting industrial gases.

FIG. 2 illustrates a process 200 of detecting industrial gases. Specifically, the computing device 102 identifies a first gas level of a gas at a first location at a first time (202). Specifically, the computing device 102 receives gas levels of one or more gases proximate to the location of each of the respective sensors 160. For example, the gas sensor 160a detects a first gas level 120 of a gas at a first location of the gas sensor 160a at a first time $t_1$. The gas sensor 160a transmits the first gas level 120 of the gas at the first location of the gas sensor 160a at the first time $t_1$ to the computing device 102.

The computing device 102 determines whether the first gas level 120 of the gas is above a first threshold (204). If the first gas level 120 is not above the first threshold, the process 200 continues back to step 202. Further, the computing device 102 can determine that the first gas level 120 of the gas is above the threshold, and store data 170 at the data store 106 indicating the first gas level 120, the location of the detected first gas level 120 (the location of the gas sensor 160a), and the time $t_1$ (206).

Further, in response to determining that the first gas level 120 of the gas is above the first threshold, the computing device 120 can identify a second gas level of the gas at a second location at a second time (208). Specifically, the computing device 102 receives gas levels of one or more gases proximate to the location of each of the respective sensors 162, and in particular, the sensor 162 that is associated with the sensor 160 that detected the first gas level 120 of the gas at the first location of step 202. For example, the gas sensor 162a detects a second gas level 122 of the gas at a second location of the gas sensor 162a at a second time $t_2$. The gas sensor 162a transmits the second gas level 122 of the gas at second first location of the gas sensor 162a at the second time $t_2$ to the computing device 102.

The computing device 102 can determine whether the second gas level 122 of the gas is above a second threshold (210). The computing device 102 can determine that the second gas level 122 of the gas is below the second threshold, and in response to determining that the second gas level 122 of the gas being below the second threshold, the computing device 102 can provide an alert 180 indicating that the first gas level 120 is above the first threshold (212). For example, the alert 180 can be an auditory alert provided across a speaker system of the facility 150. In some examples, the alert 180 can be a visual alert provided on a graphical user interface (GUI) of one or more monitored computer displays. In some examples, the alert 180 can be provided as a notification on a mobile computing device. Further, in response to determining that the second gas level 122 of the gas being below the second threshold, the computing device 102 can store data 170 at the data store 106 indicating the second gas level 122, the location of the detected second gas level 120 (the location of the gas sensor 162a), and the time $t_2$ (214).

The computing device 102 can determine that the second gas level 122 of the gas is above the second threshold. In response to determining that the second gas level 122 of the gas being above the second threshold, the computing device 102 can store data 170 at the data store 106 indicating the second gas level 122, the location of the detected second gas level 120 (the location of the gas sensor 162a), and the time $t_2$ (216). Additionally, in response to determining that the second gas level 122 of the gas is above the second threshold, the computing device 102 can calculate a difference between the second time $t_2$ and the first time $t_1$ (218).

The computing device 102 determines whether the difference between the second time $t_2$ and the first time $t_1$ is positive (220). In some examples, the computing device 102 determines that the difference between the second time $t_2$ and the first time $t_1$ is positive ($t_2 > t_1$), and in response, determines that the first location is the source of the gas (222). That is, the computing device 102 determines that the first location of the gas sensor 160a to be a source of the gas. The computing device 102 further provides the alert 180 indicating the first location as the source of the gas (224).

In some examples, the computing device 102 determines that the difference between the second time $t_2$ and the first time $t_1$ is negative ($t_2 < t_1$), and in response, determines that the second location is the source of the gas (226). That is, the computing device 102 determines that the second location of the gas sensor 162a to be a source of the gas. The computing device 102 further provides the alert 180 indicating the second location as the source of the gas (228).

Figure 4:
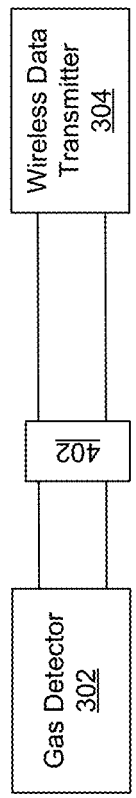
FIG. 4 is a wiring diagram of the gas detection system.
Figure 3:
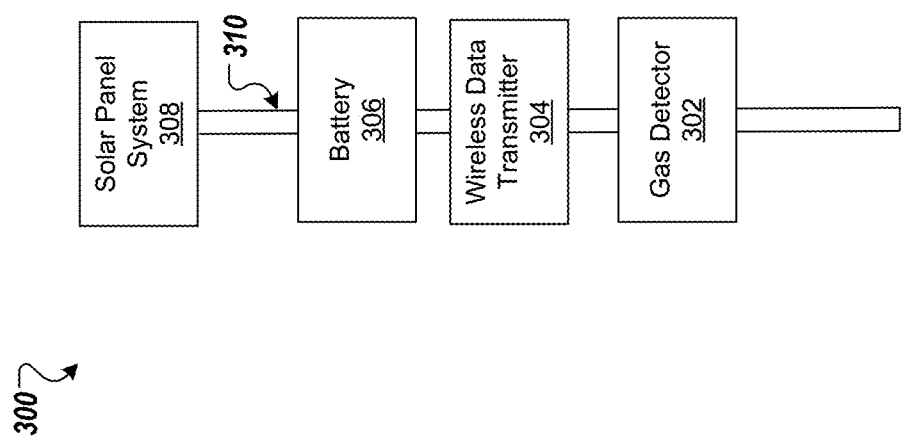
FIG. 3 illustrates a gas detection system.
Figure 5:
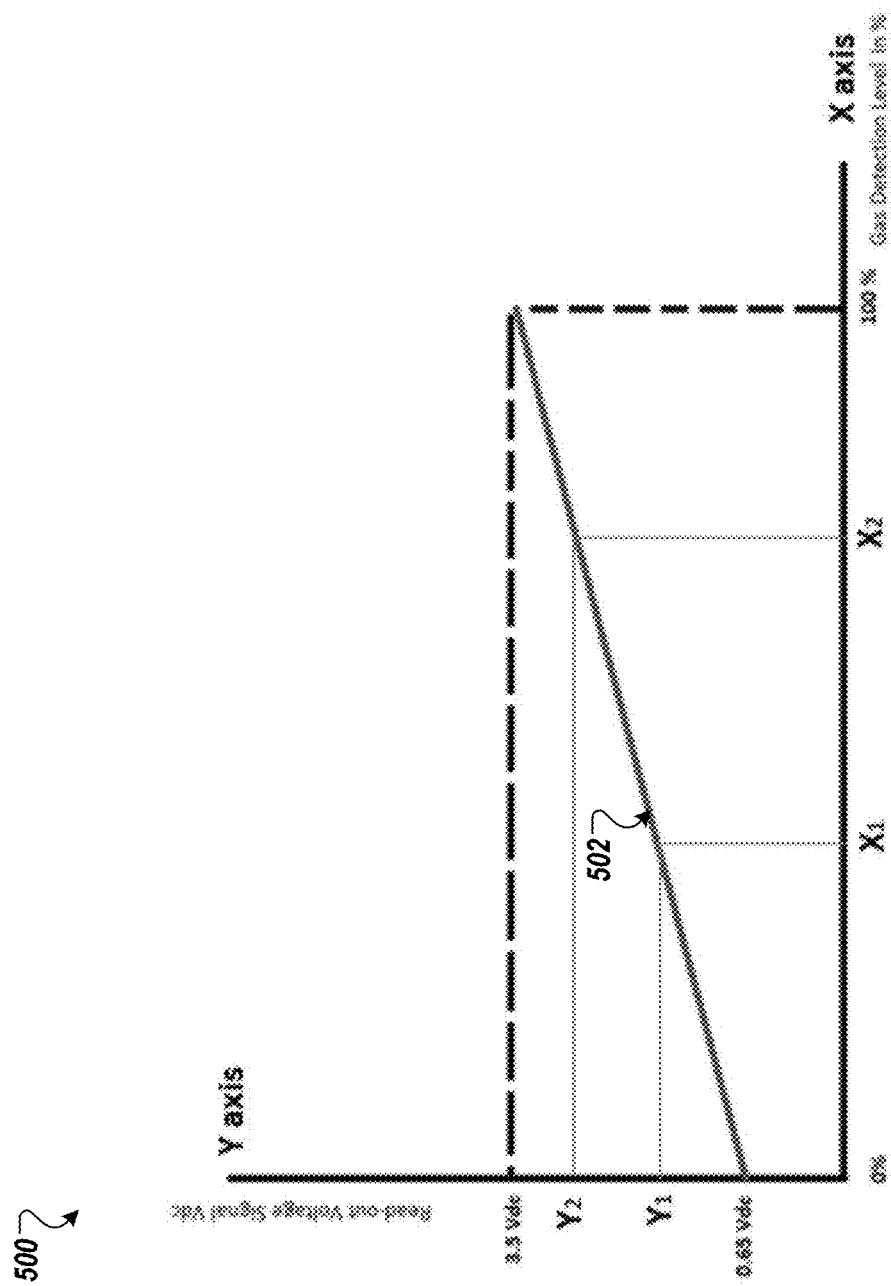
FIG. 5 is graph of the output voltage of the gas detection system for detection of gas levels.

FIG. 3 illustrates a gas detection system 300, for example, one of the gas sensors 160, 162 of FIG. 1. The gas sensor system 300 includes a gas detector 302, a wireless data transmitter 304, a battery 306, and a solar panel system 308 all physically coupled to a post assembly 310. The solar panel system 308 can be in electrically coupled to the battery 306 to store energy obtained by the solar panel system 308 within the battery 306. The battery 306 can further be coupled to the gas detector 302 and the wireless data transmitter 304 to provide power to the same. The gas detector 302 can be an industrial-type gas sensor with a 0 to 20 milli-amp (mA) output signal, for example, a General Monitors industrial LEL sensor, model S4000CH. The wireless data transmitter 304 can include an Xbee Model S1 Series that is connected in parallel with a resistor 402, as illustrated by the wiring diagram 400 in FIG. 4. In some examples, the resistor 402 has a value of 175 ohms. Following the wiring diagram 400, the output of the gas sensor 302 of 0 to 20 mA is converted to a voltage signal between 0 and 3.5 volts (DC). In general, the detected gas levels of the gas by the gas detector 302 is linearly related to the output voltage signal of the gas detector 302, as shown by the graph 500 in FIG. 5. For example, for an output voltage of the gas detector 302 of 0.65 volts indicates a 0% of the gas in the ambient air sample, and an output voltage of the gas detector 302 of 3.5 volts indicates a 100% of the gas in the ambient air sample. The slope of the linear relationship line 502 is the ratio of the difference between two y-axis points ($y_2$ and $y_1$) and the difference between two x-axis points ($x_2$ and $x_1$).

In some examples, the gas sensor system 300 can be mobile—that is, the gas sensor system 300 is not stationary. For example, the gas sensory system 300 can be mounted on a vehicle that monitors the facility 150. The gas sensor system 300 can transmit gas level readings wireless to a receiving station (not shown), for example, when the vehicle pass through one or more wireless receiving station processing areas/zones.

Figure 6:
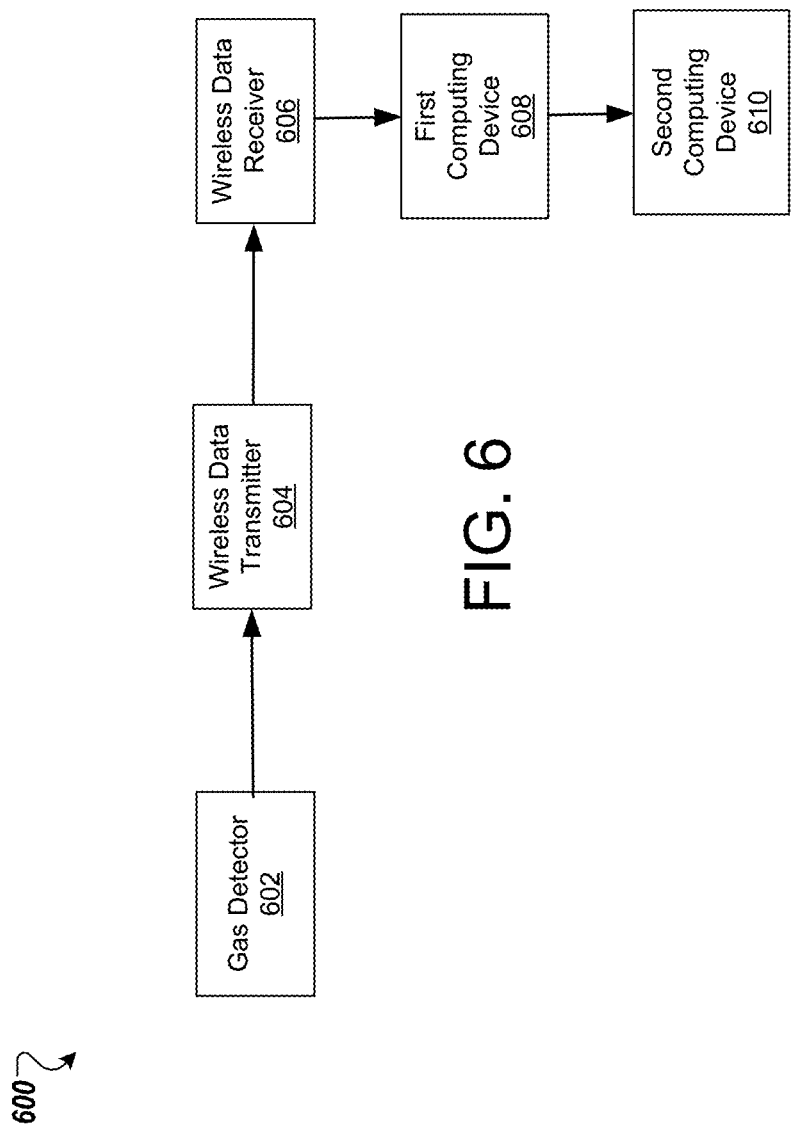
FIG. 6 is a schematic illustration of a system for a mobile gas sensor system.

Referring to FIG. 6, a system 600 is shown for mobile gas sensor systems. Specifically, the system 600 includes a gas detector 602, a wireless data transmitter 604, a wireless signal receiver 606, a first computing device 608, and a second computing device 610. The gas detector 602 and the wireless data transmitter 604 can be similar to the gas detector 302 and the wireless data transmitter 304, respectively, of FIG. 3. The wireless data transmitter 604 can be wireless coupled with the wireless signal receiver 606 to provide data of detected gas levels. The wireless signal receiver 606 can provide the data to the first computing device 608. The first computing device 608 can process the data of the detected gas levels, including converting the signal to digital, activating an alert, displaying gas level percentage in a LCD display, providing gas level percentage through an output communications channel (USB port serial), and enable silence button to deactivate alarm. In some examples, the first computing device is an Arduino Mega Board. The second computing device 610 can further process the data of the detected gas levels, including providing storing of the gas level data, providing machine to machine communications to provide the alerts over e-mails and radio terminals, and host system supervision websites to reflect online gas levels. In some examples, the second computing device 610 can include a Raspberry Pi 3 Board.

Figure 7:
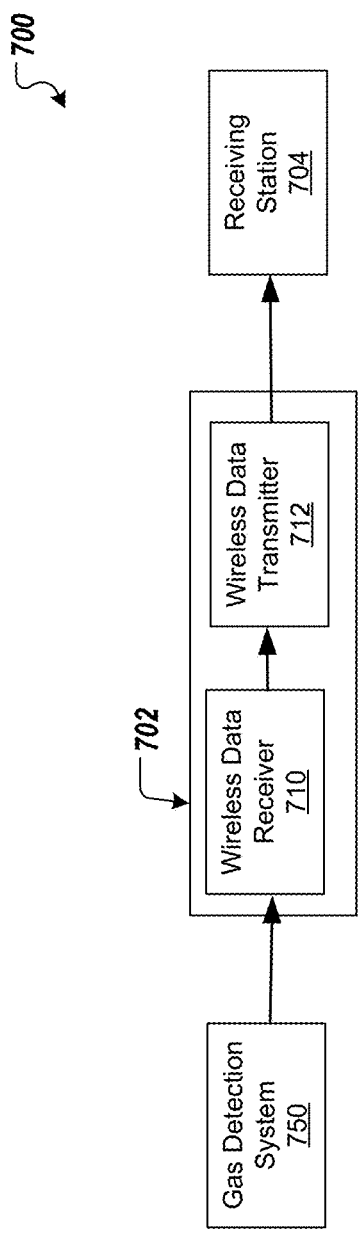
FIG. 7 is a schematic illustration of a wireless signal regenerator system.

In some implementations, referring to FIG. 7, a gas detection system 750, similar to the gas detection 300 of FIG. 3, can be coupled to a wireless signal regenerator system 700. Specially, the wireless signal regenerator system 700 can include a wireless signal range extender 702 and a system wireless receiving station 704; however, the system 700 can include any number of wireless signal range extenders. To that end, the wireless signal range extender 702 can repeat the signal provided by the gas detection system 300 such that the system wireless receiving station 704 detects such signal. This signal can be repeated multiple times for each wireless signal range extender, for example, 100 to 500 meters. The wireless signal range extender 702 includes a wireless data receiver 710 to receive the signal from the gas detection system 300 and a wireless data transmitter 712 to transmit the signal to the system wireless receiving station 704.

Figure 8:
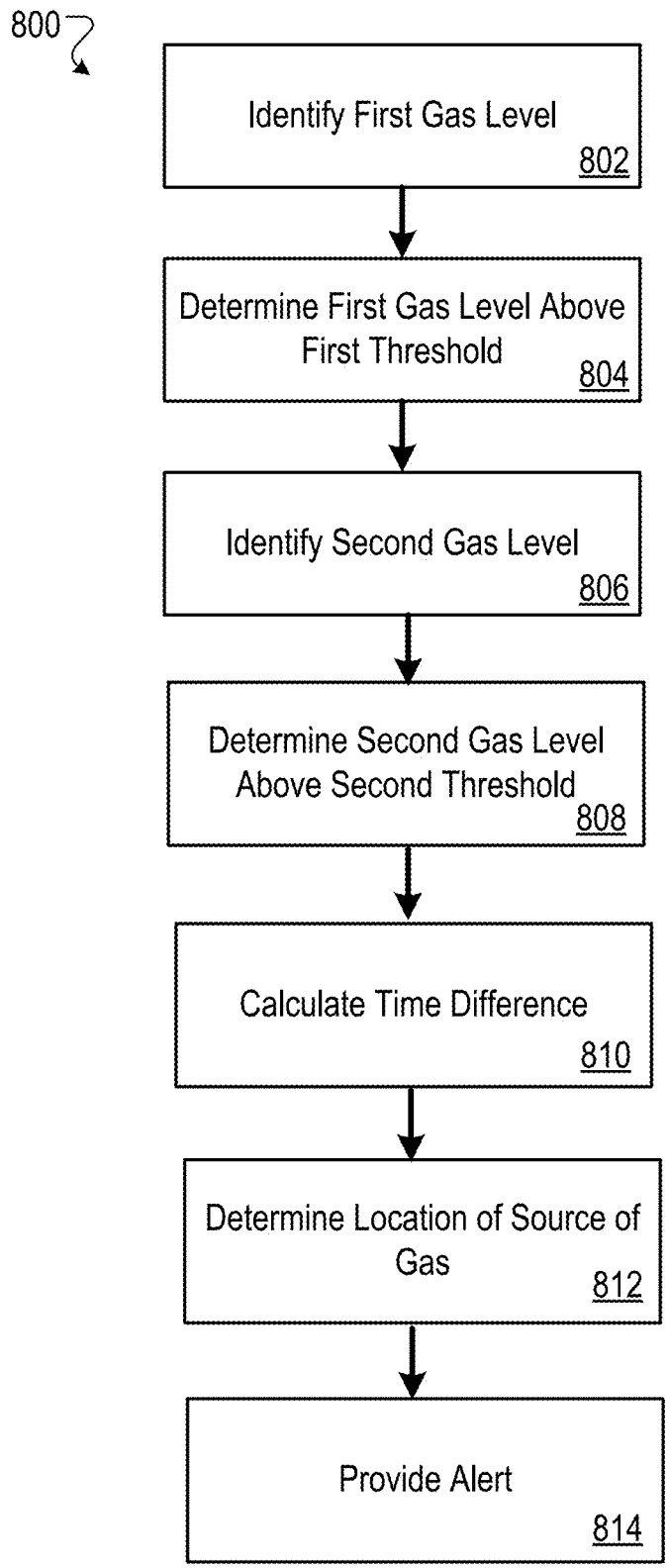
FIG. 8 illustrates a flowchart for detecting industrial gases.

FIG. 8 illustrates a flow chart that illustrates a method for detecting industrial gases. For clarity of presentation, the description that follows generally describes method 800 in the context of FIGS. 1-7. For example, as illustrated, particular steps of the method 800 may be performed on or at the computing system 100. However, method 800 may be performed, for example, by any other suitable system, environment, software, and hardware, or a combination of systems, environments, software, and hardware as appropriate. Operations of method 800 can include one or more optional steps, including only one or more of the steps being performed, and further, that the steps of FIG. 8 can be performed in any order.

The computing device 102 identifies a first gas level 120 of a gas at a first location at a first time $t_1$ (802). For example, the first location can be a location of the gas sensor 160a that detects the gas at the first time $t_1$. The computing device 102 determines that the first gas level 120 of the gas is above a first threshold (804). The computing device 102, in response to determining that the first gas level 120 of the gas is above the first threshold, identifies a second gas level 122 of the gas at a second location at a second time $t_2$ (806). For example, the second location can be a location of the gas sensor 162a that detects the gas at the second time $t_2$. The computing device 102 determines that the second gas level 122 of the gas is above a second threshold (808). The computing device 102, in response to determining that the second gas level 122 of the gas is above the second threshold, calculates a difference between the second time $t_2$ and the first time $t_1$ (810). The computing device 102, based on the difference between the second time $t_2$ and the first time $t_1$, determines that one of the first location and the second location as a source of the gas (812). The computing device 102 provides an alert 180 based on determining the location of the source of the gas (814).

Figure 9:
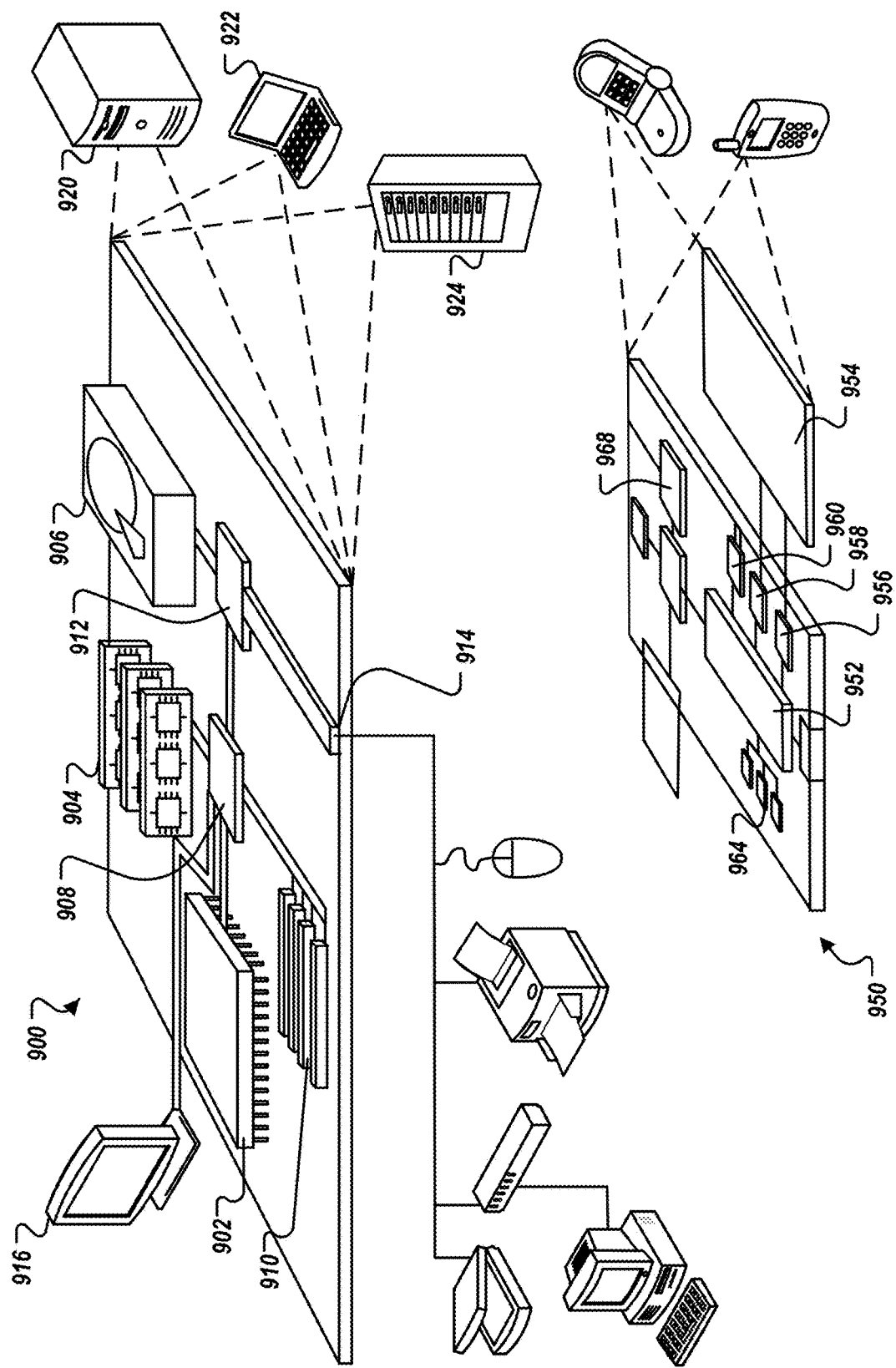
FIG. 9 illustrates an example computing environment for implementing the techniques described herein.

FIG. 9 shows an example of a generic computer device 900 and a generic mobile computer device 950, which may be used with the techniques described here. Computing device 900 is intended to represent various forms of digital computers, such as laptops, desktops, workstations, personal digital assistants, servers, blade servers, and mainframes. Computing device 950 is intended to represent various forms of mobile devices, such as personal digital assistants, cellular telephones, and smartphones. The components shown here, their connections and relationships, and their functions, are meant to be exemplary only and are not meant to limit implementations of the inventions described in this document.

Computing device 900 includes a processor 902, memory 904, a storage device 906, a high-speed interface 908 connecting to memory 904 and high-speed expansion ports 910, and a low speed interface 914 connecting to low speed bus 914 and storage device 906. Each of the components 902, 904, 906, 908, 910, and 914, are interconnected using various busses, and may be mounted on a common motherboard or in other manners as appropriate. The processor 902 may process instructions for execution within the computing device 900, including instructions stored in the memory 904 or on the storage device 906 to display graphical information for a graphical user interface (GUI) on an external input/output device, such as display 918 coupled to high speed interface 908. In other implementations, multiple processors, and multiple buses, or both, may be used, as appropriate, along with multiple memories and types of memory. Also, multiple computing devices 900 may be connected. Each computing device can provide portions of the necessary operations (for example, as a server bank, a group of blade servers, or a multi-processor system).

The memory 904 stores information within the computing device 900. In one implementation, the memory 904 is a volatile memory unit or units. In another implementation, the memory 904 is a non-volatile memory unit or units. The memory 904 may also be another form of computer-readable medium, such as a magnetic or optical disk.

The storage device 906 is capable of providing mass storage for the computing device 900. In one implementation, the storage device 906 may be or contain a computer-readable medium, such as a floppy disk device, a hard disk device, an optical disk device, or a tape device, a flash memory or other similar solid state memory device, or an array of devices, including devices in a storage area network or other configurations. A computer program product may be tangibly embodied in an information carrier. The computer program product may also contain instructions that, when executed, perform one or more methods. The information carrier is a computer- or machine-readable medium, such as the memory 904, the storage device 906, or a memory on processor 902.

The high speed controller 908 manages bandwidth-intensive operations for the computing device 900. The low speed controller 914 manages lower bandwidth-intensive operations. Such allocation of functions is exemplary only. In one implementation, the high-speed controller 908 is coupled to memory 904, display 918 (for example, through a graphics processor or accelerator), and to high-speed expansion ports 910, which may accept various expansion cards (not shown). In the implementation, low-speed controller 914 is coupled to storage device 906 and low-speed expansion port 914. The low-speed expansion port, which may include various communication ports (for example, USB (Universal Serial Bus), Bluetooth, Ethernet, wireless Ethernet) may be coupled to one or more input/output devices, such as a keyboard, a pointing device, a scanner, or a networking device such as a switch or router, for example, through a network adapter.

The computing device 900 may be implemented in a number of different forms, as shown in the figure. For example, it may be implemented as a standard server 920, or multiple times in a group of such servers. It may also be implemented as part of a rack server system 924. In addition, it may be implemented in a personal computer such as a laptop computer 922. Alternatively, components from computing device 900 may be combined with other components in a mobile device (not shown), such as device 950. Each of such devices may contain one or more of computing device 900, 950, and an entire system may be made up of multiple computing devices 900, 950 communicating with each other.

Computing device 950 includes a processor 952, memory 964, an input/output device such as a display 954, a communication interface 960, and a transceiver 968, among other components. The device 950 may also be provided with a storage device, such as a microdrive or other device, to provide additional storage. Each of the components 950, 952, 964, 954, 960, and 968, are interconnected using various buses, and several of the components may be mounted on a common motherboard or in other manners as appropriate.

The processor 952 may execute instructions within the computing device 950, including instructions stored in the memory 964. The processor may be implemented as a chipset of chips that include separate and multiple analog and digital processors. The processor may provide, for example, for coordination of the other components of the device 950, such as control of user interfaces, applications run by device 950, and wireless communication by device 950.

Processor 952 may communicate with a user through control interface 958 and display interface 956 coupled to a display 954. The display 954 may be, for example, a TFT LCD (Thin-Film-Transistor Liquid Crystal Display) or an OLED (Organic Light Emitting Diode) display, or other appropriate display technology. The display interface 956 may comprise appropriate circuitry for driving the display 954 to present graphical and other information to a user. The control interface 958 may receive commands from a user and convert them for submission to the processor.

What is claimed is:
1. A computer-implemented method, comprising:
identifying, using a first sensor at a first geographic location, a first gas level of a gas at the first geographic location at a first time;
determining that the first gas level of the gas is above a first threshold;
in response to determining that the first gas level of the gas is above the first threshold, identifying, using a second sensor at a second geographic location, a second gas level of the gas at the second geographic location at a second time, wherein the first geographic and second geographic locations are different;
determining that the second gas level of the gas is above a second threshold;
in response to determining that the second gas level of the gas is above the second threshold, calculating a difference between the second time and the first time;
based on the difference between the second time and the first time, determining that one of the first geographic location and the second geographic location is a source of the gas; and
providing an alert based on determining the location of the source of the gas.

2. The method of claim 1, wherein calculating the difference between the second time and the first time includes determining that the difference is positive, the method further comprising:
in response to determining that the difference is positive, determining that the first geographic location is the source of the gas; and
providing the alert indicating that the first geographic location is the source of the gas.

3. The method of claim 1, wherein calculating the difference between the second time and the first time includes determining that the difference is negative, the method further comprising:
in response to determining that the difference is negative, determining that the second geographic location is the source of the gas; and
providing the alert indicating that the second geographic location is the source of the gas.

4. The method of claim 1, further comprising:
determining that the second gas level of the gas is below the second threshold; and
in response to determining that second gas level of the gas is below the second threshold, providing an alert indicating that the first gas level is above the first threshold.

5. The method of claim 1, wherein the alert is an auditory alert.

6. The method of claim 1, wherein the gas includes hydrogen sulfide.

7. The method of claim 1, further comprising storing, in a data store, data indicating i) the first geographic location and the first gas level of the gas and ii) the second geographic location and the second gas level of the gas.

8. The method of claim 1, wherein the first and second gas levels are respective percentages of the gas in a sampled quantity of ambient air.

9. The method of claim 1, wherein the first sensor and the second sensor respectively wirelessly send the first gas level and the second gas level to a gas detection computing unit.

10. A system, comprising:
one or more processors; and
a non-transitory computer-readable storage medium coupled to the one or more processors and storing programming instructions for execution by the one or more processors, the programming instructions instruct the one or more processors to perform operations comprising:

identifying, using a first sensor at a first geographic location, a first gas level of a gas at the first geographic location at a first time;

determining that the first gas level of the gas is above a first threshold;

in response to determining that the first gas level of the gas is above the first threshold, identifying, using a second sensor at a second geographic location, a second gas level of the gas at the second geographic location at a second time, wherein the first geographic and second geographic locations are different;

determining that the second gas level of the gas is above a second threshold;

in response to determining that the second gas level of the gas is above the second threshold, calculating a difference between the second time and the first time;

based on the difference between the second time and the first time, determining that one of the first geographic location and the second geographic location is a source of the gas; and providing an alert based on determining the location of the source of the gas.

11. The system of claim 10, wherein calculating the difference between the second time and the first time includes determining that the difference is positive, the operations further comprising:

in response to determining that the difference is positive, determining that the first geographic location is the source of the gas; and providing the alert indicating that the first geographic location is the source of the gas.

12. The system of claim 10, wherein calculating the difference between the second time and the first time includes determining that the difference is negative, the operations further comprising:

in response to determining that the difference is negative, determining that the second geographic location is the source of the gas; and providing the alert indicating that the second geographic location is the source of the gas.

13. The system of claim 10, the operations further comprising:

determining that the second gas level of the gas is below the second threshold; and in response to determining that second gas level of the gas is below the second threshold, providing an alert indicating that the first gas level is above the first threshold.

14. The system of claim 10, wherein the alert is an auditory alert.

15. The system of claim 10, wherein the gas includes hydrogen sulfide.

16. The system of claim 10, the operations further comprising storing, in a data store, data indicating i) the first geographic location and the first gas level of the gas and ii) the second geographic location and the second gas level of the gas.

17. A non-transitory computer readable medium storing instructions to cause one or more processors to perform operations comprising:

identifying, using a first sensor at a first geographic location, a first gas level of a gas at the first geographic location at a first time;

determining that the first gas level of the gas is above a first threshold;

in response to determining that the first gas level of the gas is above the first threshold, identifying, using a second sensor at a second geographic location, a second gas level of the gas at the second geographic location at a second time, wherein the first geographic location differs from the second geographic location;

determining that the second gas level of the gas is above a second threshold;

in response to determining that the second gas level of the gas is above the second threshold, calculating a difference between the second time and the first time;

based on the difference between the second time and the first time, determining that one of the first geographic location and the second geographic location is a source of the gas; and providing an alert based on determining the location of the source of the gas.

18. The computer readable medium of claim 17, wherein calculating the difference between the second time and the first time includes determining that the difference is positive, the operations further comprising:

in response to determining that the difference is positive, determining that the first geographic location is the source of the gas; and providing the alert indicating that the first geographic location is the source of the gas.

19. The computer readable medium of claim 17, wherein calculating the difference between the second time and the first time includes determining that the difference is negative, the operations further comprising:

in response to determining that the difference is negative, determining that the second geographic location is the source of the gas; and providing the alert indicating that the second geographic location is the source of the gas.

20. The computer readable medium of claim 17, the operations further comprising:

determining that the second gas level of the gas is below the second threshold; and in response to determining that second gas level of the gas is below the second threshold, providing an alert indicating that the first gas level is above the first threshold.

* * * * *